United States Patent [19]

Mitsugi et al.

[11] 4,370,414

[45] Jan. 25, 1983

[54] PROCESS FOR PRODUCING 6-AMINOPENICILLANIC ACID AND 6-AMINOPENICILLANIC ACID S-OXIDE

[75] Inventors: Takashi Mitsugi, Izumiotus; Ryonosuke Muneyuki, Kyoto; Yoshiharu Wakisaka, Takarazuka; Kenzo Koizumi, Sakai; Eiji Kondo, Ikeda, all of Japan

[73] Assignee: Shionogi & Co., Ltd., Osaka, Japan

[21] Appl. No.: 194,277

[22] Filed: Oct. 6, 1980

[30] Foreign Application Priority Data

Oct. 30, 1979 [JP] Japan .................................. 54-140928

[51] Int. Cl.$^3$ .......................... C12P 37/06; C12R 1/06
[52] U.S. Cl. ........................................ 435/44; 435/830
[58] Field of Search .................................. 435/44, 830

[56] References Cited

U.S. PATENT DOCUMENTS

| | | | |
|---|---|---|---|
| 3,116,218 | 12/1963 | Kaufmann et al. | 435/44 |
| 3,239,428 | 3/1966 | Tozokawa et al. | 435/44 |
| 3,446,705 | 5/1969 | Heuser et al. | 435/44 |
| 3,925,155 | 12/1975 | Kondo et al. | 435/44 |

*Primary Examiner*—Alvin E. Tanenholtz
*Attorney, Agent, or Firm*—Wenderoth, Lind & Ponack

[57] ABSTRACT

A process for producing 6-aminopenicillanic acid and 6-aminopenicillanic acid S-oxide by means of enzymes produced by microbes belonging to Arthrobacter genus, especially *Arthrobacter cremorum* and *Arthrobacter flagellum*.

4 Claims, No Drawings

PROCESS FOR PRODUCING 6-AMINOPENICILLANIC ACID AND 6-AMINOPENICILLANIC ACID S-OXIDE

This invention relates to a process for producing 6-aminopenicillanic acid or 6-aminopenicillanic acid S-oxide by means of enzymes produced by microbes belonging to Arthrobacter genus.

Various processes for producing 6-aminopenicillanic acid from penicillins by means of enzymes produced by bacteria or fungi have been studied. Especially, there are well known processes by means of bacteria belonging to Escherichia, Bacillus, Pseudomonas, Proteus and Micrococcus genera, or the like.

The present inventors investigated to find a simple enzymatic process for producing 6-aminopenicillanic acid or 6-aminopenicillanic acid S-oxide from benzylpenicillin or benzylpenicillin S-oxide in high yield, so that they found the foregoing object was achieved by means of a microbe belonging to Arthrobacter genus and completed this invention.

Processes for producing 6-aminopenicillanic acid from penicillins by means of a microbe belonging to Arthrobacter genus have already been disclosed in U.S. Pat. No. 3,116,218 wherein Ar. strain NRRL B-2743 is used. Japanese Examined Patent Publication Nos. 45-950 and 50-2758 disclose enzymatic methods using *Ar. viscosus* and *Ar. simplex* No. 3151, respectively.

A process for producing 6-aminopenicillanic acid S-oxide by enzymatic means is, however, not known yet. The microbes of this invention are different in characteristics from the microbes disclosed in the foregoing references as mentioned below, so the microbes of this invention are identified as new species. The strains M-1376-2 and M-2183-1 isolated from a soil sample by the present inventors have the following characteristics.

M-1376-2

A. Morphology and Stainability (1) Vegetative cell (Gly-IM agar medium* and Nutrient agar medium)

Short rods ($0.6$–$0.7 \times 0.8$–$2.0\mu$) and a few pleomorphisms are observed at early stage of fermentation (1 day stage of fermentation, 28° C.). Most cells become coccoid ($0.6$–$0.8 \times 0.8$–$1.0\mu$) at late stage (28° C., 4 to 8 days) and many beaded cells are observed. Many swollen bodies (probably be Arthrospore) ($0.8$–$1.2\mu$, spherule) are observed at 37° C. after 2 days stage.
(* Gly-IM agar: glycerol 0.5%, polypeptone 0.25%, yeast extract 0.25%, meat extract 0.25%, Difco soytone 0.25%, salt 0.3%, agar 1.25% (pH 7.0))

(2) Gram Stain: Postive (Nutrient agar medium, 28° C., 1 to 8 days)
(3) Flagellum: None
(4) Motility: Not observed
(5) Spore: None

B. Growth Characteristics (1) Colony (Nutrient agar medium, 28° C.)

Circular (1-2 mm, 4 days), convex, entire colonies with shining smooth surface. A grayish white color, semiopaque density and soft structure.

(2) Growth on agar slant (Nutrient agar medium, 28° C., 1-2 days)

Moderate filiform growth with shining surface. Creamy grayish white color, opaque density and soft structure.

(3) Growth on liquid medium (Gly-IM medium, 28° C.)

Moderate uniform growth. Some precipitation occurs at late stage. No pellicle is formed but a ring is observed at 7 days stage or later.

C. Conditions for Growth (1) Oxygen requirement: Complete aerobic
(2) Temperature for Growth (Gly-IM): Good growth is observed at 20° to 33.5° C. The growth rate becomes maximum at 27.5° to 30.5° C. On agar slant, a visible growth is observed at 37° C. on the first day and at 10° C. at the third day and later.
(3) pH range for Growth: Good growth is seen at pH 6.28 to 10.11. The optimum pH for growth is at pH 7.42 to 8.10.

D. Physiological Characteristics (1) Catalase: Positive
(2) Kovac's oxidase test: Positive
(3) VP test: Negative (28° C.)
(4) MR test: Negative (28° C.)
(5) Egg yolk reaction: Negative
(6) Reduction of nitrate: Positive
(7) Hydrogen sulfide formation: Positive (weakly)
(8) Indole formation: Negative
(9) Urease: Positive
(10) Gelatin liquefaction: Positive
(11) Casein hydrolysis: Positive
(12) Starch hydrolysis: Positive (dextrin stored)
(13) Milk reaction:
   Peptonization: Positive
   Acid formation: Negative
   Coagulation: Positive (slightly)
(14) Acid formation from sugars: No acid formation is observed from the following sugars: L-arabinose, D-xylose, rhamnose, D-ribose, D-glucose, D-mannose, D-galactose, D-fructose, sucrose, maltose, lactose, trehalose, raffinose, melibiose, dextrin, starch, glycogen, inulin, glycerol, adonitol, mannitol, sorbitol, dulcitol, salicin, α-methylglucoside, and m-inositol.
(15) Cellulose decomposition: Negative

E. Amino acids and sugars composing cell walls

A purified cell wall sample prepared in a manner by Kotani et al. (Journal of Nara Medical Association, vol. 10, 45 (1959)) was hydrolyzed in a conventional manner. The resultant sugars were trimethylsilylated. The sample was subjected to amino acid analysis and gas chromatography. As shown in Table 1, lysine, alanine, and glutamic acid were main amino acid components. Glucose and mannose were contained as sugar component, but no galactose was detected. No Arabinose was contained.

F. Nutrient requirement

Vitamine $B_1$ is required.

M-2183-1

A. Morphology and Stainability (1) Vegetative cells (Gly-IM agar medium and nutrient agar medium):

Short rods and coccus ($0.4$–$0.6 \times 0.8$–$2.0\mu$) are observed at 1 day stage (28° C.). Most cells become coccoid ($0.5$–$0.6 \times 0.6$–$0.8\mu$) at 2 days stage or later and many beaded cells are observed. Swollen bodies (Arthrospore) (0.8–1.0μ, spherule) are observed at 4 days stage or later at 37° C.

(2) Gram Strain: Positive (Nutrient agar medium, 28° C., 1 to 8 days)

(3) Flagellum: Observed (4) Motility: Observed (5) Spore: None

B. Growth Characteristics (1) Colony (Nutrient agar medium, 28° C.)

Circular (0.3–1.5 mm, at 4 days stage), convex, entire colonies with shining smooth surface. Grayish white color, semitransparent density, and soft to butyrous structure.

(2) Growth on agar slant (Nutrient agar medium, 28° C., 1–2 days)

Moderate filiform growth with shining surface. Grayish white color, semitransparent density and soft structure.

(3) Growth on liquid medium (Gly-IM medium, 28° C.)

Moderate uniform growth. Some precipitation occurs at late stage. No pellicle is formed but a ring is observed at 7 days stage or later.

C. Conditions for Growth (1) Oxygen requirement: Complete aerobic (2) Temperature for Growth (Gly-IM medium)

Good growth is seen at 18.5° to 37° C. The rapidest growth is observed at 27.5° to 35.5° C. On agar slant, a visible growth is observed at 10° C. on the second day and at 37° C. on the first day.

(3) pH range for Growth: Good growth is seen at pH 6.28 to 10.1. The optimum pH for growth is at pH 7.42 to 8.10.

D. Physiological Characteristics (1) Catalase: Positive (2) Kovac's Oxidase test: Negative (3) VP test: Negative (28° C.)

(4) MR test: Negative (28° C.)

(5) Egg yolk reaction: Negative (6) Reduction of nitrate: Positive (7) Hydrogen sulfide formation: Positive (weakly)

(8) Indole formation: Negative (9) Urease: Positive

(10) Gelatin liquefaction: Positive

(11) Casein hydrolysis: Positive

(12) Starch hydrolysis: Negative

(13) Milk reaction:
   Peptonization: Positive
   Acid formation: Negative
   Coagulation: Positive (slightly)

(14) Acid formation from sugars: No acid formation is observed from the following sugars:

L-arabinose, D-xylose, rhamnose, D-ribose, D-glucose, D-mannose, D-galactose, D-fructose, sucrose, maltose, lactose, trehalose, raffinose, melibiose, dextrin, starch, glycogen, inulin, glycerol, adnitol, mannitol, sorbitol, dulcitol, salicin, α-methylglucoside, and m-inositol

(15) Cellulose decomposition: Negative

E. Amino acids and sugars composing cell walls

The composition was determined in the same manner as in M-1376-2. The result is shown in Table 1. Lysine, alanine, and glutamic acid were main amino acid components. Glucose and mannose were contained with galactose as sugar component but no arabinose detected.

F. Nutrient requirement

Vitamin $B_1$ and methionine are required.

The characteristics shown above were compared with those of the following species belonging to the same genus:

*Arthrobacter globiformis,*
*Arthrobacter simplex,*
*Arthrobacter tumescens,*
*Arthrobacter citreus,*
*Arthrobacter terregens,*
*Arthrobacter flavescens,*
*Arthrobacter duodecadis,*

[The above 7 species are described in Bergy's Manual of Determinative Bacteriology, 8th edition (1974)]

*Arthrobacter luteus,* [described in J. Gen. Appln. Microbial., 15, 317–326 (1969)]

*Arthrobacter marinus,* [described in J. Gen. Microbiol., 62, 159–169 (1970)]

*Arthrobacter viscosus,* [described in J. Bact., 90(1), 147–150 (1965)]

*Arthrobacter polychromogenes,* [described in J. Microbiol. Serol., 29, 1–15 (1963)]

*Arthrobacter conscciatus,* [described in Ann. Inst. Pasteur. 101, 793–800 (1963)]

*Arthrobacter nicotinoborus,* [described in Hoppe-Seyler's Z. Physiol. Chem. 337, 282–283 (1964)] and

*Arthrobacter varialilux,* [described in Z. Bakt. Parasit. Infektioskr. Hyg. Art II, 114, 520–537 (1961)].

As the result, both the strains were not considered to belong to the same species. Moreover, regarding to *Ar. globiformis* (ATCC No. 8010) and *Ar. simplex* (ATCC No. 6946) the amino acids and sugars composing cell walls were investigated and found to be distinguished from those of M-1376-2 and M-2183-1 (see Table 1).

Therefore, it is concluded that the two microbes belong to new species of Arthrobacter genus. The strain M-1376-2 is designated as *Arthrobacter cremorum* nov. sp. M-1376-2 and deposited with the Fermentation Research Institute, Agency of Industrial Science & Technology, Yatabe-machi, Ibaragi Pref., Japan under accession number FERM-P No. 5143. The strain M-2183-1 is designated as *Arthrobacter flagellum* nov. sp. M-2183-1 and deposited under accession number FERM-P No. 5142. Both the strains were deposited on Aug. 16, 1979. They have also been deposited with American Type Culture Collection, 12301 Parklawn Drive Rockville, Md. 20852 under accession numbers ATCC Nos. 31567 and 31566. The deposit date is Sept. 13, 1979.

This invention includes microbes belonging to *Arthrobacter cremorum* or *Arthrobacter flagellum* producing enzymes which convert benzylpenicillin into 6-aminopenicillanic acid. Additionally, this invention includes any strain of their mutants or variants as long as they produce said enzyme. Namely, this invention is effected by a strain of *Arthrobacter cremorum* or *Arthrobacter flagellum* or a mutant or a variant thereof. Further, this invention also includes microbes belonging to Arthrobacter genus producing enzyme which converts benzylpenicillin S-oxide into 6-aminopenicillanic acid S-oxide.

TABLE 1

| | Test strain | | | |
|---|---|---|---|---|
| Component | M-1376-2 | M-2183-1 | Ar. globiformis ATCC 8010 | Ar. simplex ATCC 6946 |
| Diaminopi- | o | o | o | + |

TABLE 1-continued

| Component | M-1376-2 | M-2183-1 | Ar. globiformis ATCC 8010 | Ar. simplex ATCC 6946 |
|---|---|---|---|---|
| melic acid | | | | |
| Lysine | + | + | + | o |
| Glysine | o | +0.2* | o | o |
| Aspartic acid | o | o | o | o |
| Serine | o | o | o | o |
| Glutamic acid | + | + | + | + |
| Alanine | + | + | + | + |
| Leucine | o | o | o | o |
| Glucosamine | + | + | + | + |
| Galactosamine | o | — | — | — |
| Glucose | + | + | — | — |
| Galactose | — | + | + | + |
| Mannose | + | + | — | — |
| Arabinose | — | — | — | — |
| Rhamnose | — | — | — | + |
| Unidentified sugar | — | — | — | + |

Notes:
o a minor amount;
+ main component;
— none
*The amount is about 1/5 of main component.

The process of this invention is executed as follows. In the first step, the desirable enzyme is produced from the above microbes. The above microbes are cultivated under a suitable condition for growth. The medium consists of suitable carbon sources, nitrogen sources, and inorganic salts. Examples of the carbon sources are glucose, inositol, starch, dextrin, glycerol, molasses, organic acid and the like, which may be used alone or as a mixture. Examples of the nitrogen sources are peptone, soybean meal, corn steep liquor, meat extract, yeast extract, cotton seed flour, wheat germ, ammonium sulfate, ammonium nitrate, and the like, which may be used alone or as a mixture. Examples of the inorganic salts are calcium carbonate, sodium chloride, potassium chloride, magnesium sulfate, cobalt chloride, various phosphates, and the like, which may be added to the medium as occasion demands.

The fermentation may be conducted in a conventional manner. Liquid culture is preferable. Submerged aerobic culture is preferable for a large scale production. The pH of the medium may be adjusted to about 6 to 10.5, particularly about 7.0 to 8.5. If the pH of the medium varies during the fermentation, a suitable buffering agent may be added to keep a certain pH range. The fermentation may be executed at about 20° to 40° C., preferably about 25° to 32° C. The fermentation is continued until the production of desirable enzyme reaches maximum. Ordinarily, it takes about 20 to 100 hours for the completion.

The enzymes of this invention are mainly produced outside the cell, so the intact fermentation broth may be used directly or after removal of the cells by filtration, centrifugation, or siphon, the culture broth may be employed in this invention. The above cell-removed medium may be employed directly or a crude enzyme obtained by, for example, salting-out with ammonium sulfate may be used. In order to use highly pure enzyme, the crude enzyme may further be purified by chromatography of, e.g. DEAE cellulose. The enzyme may be employed in a form adsorbed or fixed on water insoluble carriers, e.g. activated clay, celite, DEAE-Sephadex (Pharmacia), DEAE-cellulose, Sepharose 4B (Pharmacia), agar and the like.

The starting materials of this invention, benzylpenicillin and benzylpenicillin S-oxide mean 6-(phenylacetamido)penicillanic acid and the S-oxide and salts thereof (e.g. sodium, potassium, calcium, aluminium, ammonium, and substituted ammonium salts and the like).

The method of this invention is executed by contacting benzylpenicillin or the S-oxide with the above mentioned enzyme. For example, 6-aminopenicillanic acid can be obtained by adding benzylpenicillin to the culture broth, or by mixing the above enzyme solution or enzyme per se into an aqueous solution, preferably buffer solution, of benzylpenicillin or by contacting bezylpenicillin with fixed enzyme. Following the same procedure, 6-aminopenicillanic acid S-oxide may be obtained from bezylpenicillin S-oxide. The enzyme reaction may be carried out at about 30° to 40° C., preferably at about 37° C., preferably while keeping the pH at 6.5 to 9.5, particularly 7.0 to 8.5.

In general, when the same type of enzyme reaction is carried out with *Escherichia coli*, it is necessary to add phenylacetic acid as enzyme inducing agent to the reaction medium. On the contrary, in the reaction of this invention, no phenylacetic acid is required.

The objective product can be isolated from the reaction mixture in a conventional manner such as extraction, chromatography and the like. The products may be obtained in a form of salts.

Thus prepared 6-aminopenicillanic acid and 6-aminopenicillanic acid S-oxide are employed as starting materials in preparing well-known and potent penicillins or cephalosporins. Namely, 6-aminopenicillanic acid can be acylated with suitable acyl groups at the amino group of the 6-position to give the desirable penicillins in conventional manners. On the other hand, 6-aminopenicillanic acid S-oxide can be converted into useful cephalosporins or penicillins as shown in the following reaction scheme.

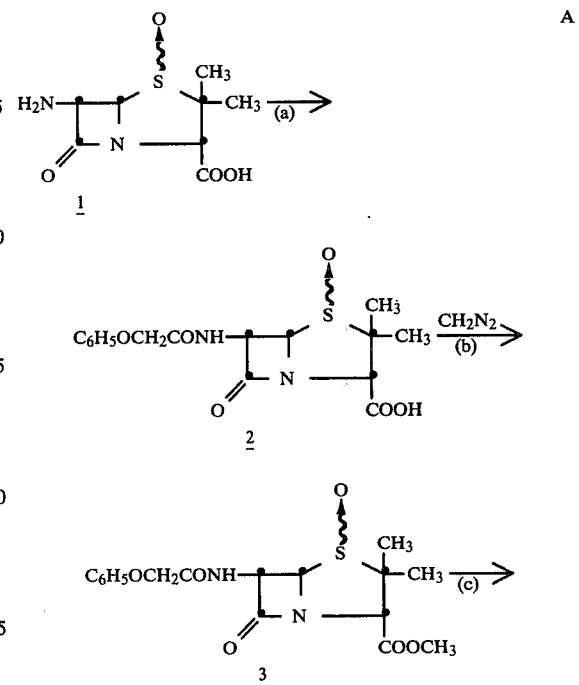

-continued

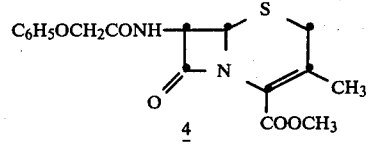

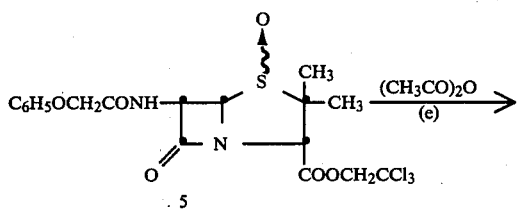

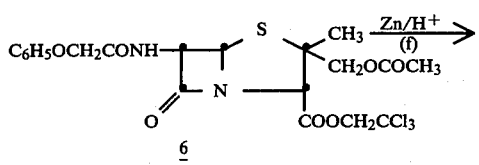

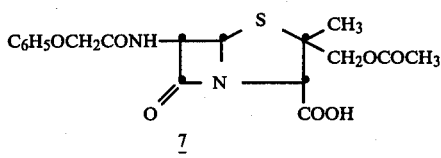

In the above Scheme A, step a, the introduction of phenoxyacetyl group into the 6-amino of 6-aminopenicillanic acid S-oxide (1), is described in Japanese Unexamined Patent Publication No. 49–5991. Step b, methyl esterification of Compound 2 is described in Journal of the American Chemical Society 91, 1401 (1969). Step c, the conversion of Compound 3 to the cephem compound is described in the above reference and Journal of Organic Chemistry 37, 793 (1972). The antibacterial activity of Compound 4 is described in the above Journal of the American Chemical Society.

In the Scheme B, step d, 2,2,2-trichloroethyl esterification of phenoxymethyl penicillin S-oxide 2, is described in "Cephalosporins and Penicillins" p. 663 (1972) (Academic press) by E. H. Flynn. Step e, introduction of acetyloxy and step f, deesterification are described in the above Journal of Organic Chemistry. The antibacterial activity of Compound 7 is described in U.S. Pat. No. 3,466,275.

The following examples are provided to further illustrate this invention. However, this invention is not limited in scope by reason of any of these examples.

EXAMPLE 1

The medium (200 ml; pH 7.0) consisting of each 0.5% of glucose, peptone, and corn steep liquor is sterilized and inoculated with *Arthrobacter flagellum* nov. sp. M-2183-1 (FERM-P No. 5142, ATCC No. 31566). Incubation is carried out at 28° C. for 3 days under agitation. A solution of 2 g of benzylpenicillin S-oxide (hereinafter, abbreviated as penicillin G S-oxide) in 5 ml of M/20 phosphate buffer solution (pH 7.0) is added to the medium and incubation is continued at 28° C. for 18 hours under agitation. Thus, 3.66 mg/ml of 6-aminopenicillanic acid S-oxide (hereinafter, abbreviated as 6-APA S-oxide) is produced (yield 55.2%). The quantitative analysis is carried out in the manner by G. E. Boxer et al (Anal. Chem. 21, 670 (1949)).

The reaction solution (200 ml) is centrifuged to remove the cells, adjusted to pH 2 with 2 N sulfuric acid, and extracted thrice with ethyl acetate to remove the unchanged starting materials and phenylacetic acid. The aqueous layer is adjusted to pH 7.0 with 2 N sodium hydroxide and mixed with 3.22 g of sodium hydrogencarbonate under ice-cooling with stirring. Phenoxyacetyl chloride (1.6 g) is gradually dropwise added thereto. The reaction mixture is treated in a conventional manner to give 780 mg of phenoxypenicillin S-oxide. Mp. 165°–168° C. (dec.)

IR: $\nu_{max}^{CHCl_3}$ 1798, 1696, 1600, 1495 cm$^{-1}$

EXAMPLE 2

To the medium which is inoculated with *Arthrobacter cremorum* nov. sp. M-1376-2 (FERM-P 5143, ATCC No. 31567) in the same manner as Example 1 is added penicillin G S-oxide at a ratio of 15 mg/ml, and the incubation is carried out at 28° C. for 22 hours. 6-APA S-Oxide is produced at the concentration of 3.15 mg/ml (yield 34.2%).

EXAMPLE 3

The medium which is inoculated with *Arthrobacter flagellum* nov. sp. M-2183-1 in the same manner as Example 1 is centrifuged to remove the cells. The supernatant (15 ml) is separated, adjusted to pH 4.5, mixed with 150 mg of celite 560, agitated for 3 hours at 4° C. to absorb the enzyme, and filtered. The resulting carrier adsorbing the enzyme is suspended in 3 ml of a 3 mg/ml solution of penicillin G S-oxide in M/20 phosphate buffer solution (pH 7.0) and the resulting suspension is agitated at 28° C. for 2.5 hours to give 1.452 mg/ml of 6-APA S-oxide (yield 73%).

EXAMPLE 4

Strongly basic anion-exchange resin Amberlite IRA-904 (Rohm & Haas Co.)(Cl type)(8 ml) which has been packed in a glass cylinder is buffered with M/100 phosphate buffer solution (pH 7.0). The supernatant (200 ml) prepared in Example 3 is passed through the above anion-exchange resin to adsorb the enzyme. The column is washed with M/20 phosphate buffer solution (pH 7.0) and then, the above buffer containing 3 mg/ml of penicillin G S-oxide is passed through the column at a rate of 9.5 ml per one hour (the inside temperature of the column is 28° C.).

In the course of the reaction, the amount of the product 6-APA S-oxide in the eluates changes between 1.68 mg/ml (yield 91.2%) and 1.746 mg/ml (yield 94.8%).

EXAMPLE 5

The cell-free medium (2.5 L) of *Arthrobacter flagellum* nov. sp. M-2183-1 is prepared by incubation in the same manner as Example 1. Ammonium sulfate is added thereto and the enzyme which is precipitated in 50 to 70% saturated solution is collected and dissolved in 20 ml of M/100 phosphate buffer solution (pH 8.0). The crude enzyme solution is obtained by dialysis against the same buffer solution at 0° C. for 24 hours.

DEAE-Sephadex (A-25)(Pharmacia)(2.4 g) is suspended in 1/100 M phosphate buffer solution (pH 8.0) and the resulting suspension is packed in a column. The above crude enzyme solution is passed through the column and fixed upon the resin, and the column is washed with M/100 to M/20 phosphate buffer solution (pH 8.0). M/20 Phosphate buffer solution (pH 8.0) containing penicillin G S-oxide at the concentration of 15 mg per 1 ml is passed through the column at a rate of 10 to 11 ml per one hour. The inner temperature of the column is kept at 28° C. The amount of 6-APA in the eluate is followed with the passage of time. The reaction is continued for 5 days to yield the enzyme in 90.3 to 97.5% yield, during which time the enzyme activity is very stable.

EXAMPLE 6

DEAE-cellulose (Watman DE 52) (8.5 g) is suspended in M/100 phosphate buffer solution (pH 8.0) and the cell-free crude enzyme solution (43.5 ml) prepared from fermentation broth (4.5 L) in the same manner as in Example 5 is added thereto. The mixture is stirred at 4° C. for 3 hours, and the resulting fixed enzyme is packed in a column. The column is washed with M/100 to M/10 phosphate buffer solution (pH 8.5). At a rate of 10.2 ml per one hour, M/10 phosphate buffer solution (pH 8.5) containing 30 mg/ml of penicillin G S-oxide is passed through the column for 30 hours. The inner temperature of the column is kept at 28° C. 6-APA S-Oxide is produced in yield of 95.8–100%.

EXAMPLE 7

The crude enzyme solution prepared in the same manner as in Example 5 is purified on a column of DEAE-cellulose. The active fraction is collected and concentrated by ultrafiltration.

4% Beaded gel agar (12 ml; wet weight 8.9 g) is activated with cyanogen bromide (J. B. C. 245, 3059 (1970)) and added to the above enzyme solution. The resulting fixed enzyme is packed in a column and washed with M/10 phosphate buffer solution (pH 8.5). At a rate of 10 to 11 ml per one hour, M/10 phosphate buffer (pH 8.5) containing 30 mg/ml of penicillin G S-oxide is passed through the column for 30 hours. The inner temperature of the column is kept at 28° C. The yield of 6-APA S-oxide is 91.2 to 96.9%.

EXAMPLE 8

The inner temperature of the agar gel column prepared in Example 7 on which enzyme is fixed is kept at 30° C. Then, M/10 phosphate buffer solution (pH 8.5) containing 30 mg/ml of benzylpenicillin is passed through the column at a rate of 8 ml per one hour. The yield of 6-aminopenicillanic acid is 80.0 to 85.5%.

What we claim is:

1. A process for producing 6-aminopenicillanic acid S-oxide which comprises contacting benzylpenicillin S-oxide with enzyme produced by a microbe belonging to Arthrobacter genus.

2. A process for producing 6-aminopenicillanic acid or 6-aminopenicillanic acid S-oxide which comprises contacting benzylpenicillin or benzylpenicillin S-oxide with enzyme produced by a strain of *Arthrobacter cremorum* or *Arthrobacter flagellum* or a mutant or a variant thereof.

3. The process of claim 2 wherein the microbe is *Arthrobacter cremorum* M-1376-2 ATCC No. 31567.

4. The process of claim 2 wherein the microbe is *Arthrobacter flagellum* M-2183-1 ATCC No. 31566.

* * * * *